US00PP25915P2

(12) United States Plant Patent
Wells

(10) Patent No.: US PP25,915 P2
(45) Date of Patent: Sep. 22, 2015

(54) *LAURUS* PLANT NAMED 'MONRIK'

(50) Latin Name: *Laurus nobilis*
Varietal Denomination: MonRik

(71) Applicant: Richard H. Wells, McMinnville, OR (US)

(72) Inventor: Richard H. Wells, McMinnville, OR (US)

(73) Assignee: Monrovia Nursery Company, Azusa, CA (US)

( * ) Notice: Subject to any disclaimer, the term of this patent is extended or adjusted under 35 U.S.C. 154(b) by 57 days.

(21) Appl. No.: 13/999,080

(22) Filed: Jan. 10, 2014

(51) Int. Cl.
*A01H 5/00* (2006.01)

(52) U.S. Cl.
USPC ..... Plt./226

(58) Field of Classification Search
USPC ..... Plt./226
CPC ..... A01H 5/12; A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Laurus* plant named 'MonRik', characterized by its compact, upright to somewhat outwardly spreading and uniformly mounded plant habit; vigorous growth habit; freely branching habit; fragrant dark green-colored leaves; and good garden performance.

1 Drawing Sheet

Botanical designation: *Laurus nobilis*.
Cultivar denomination: 'MONRIK'.

BACKGROUND OF THE INVENTION

The present invention relates to a new and distinct cultivar of *Laurus*, botanically known as *Laurus nobilis*, commonly referred to as Sweet Bay and hereinafter referred to by the name 'MonRik'.

The new *Laurus* plant originated from an open-pollination in Dayton, Oreg. of an unnamed selection of *Laurus nobilis*, not patented, as the female, or seed, parent with an unknown selection of *Laurus nobilis* as the male, or pollen, parent. The new *Laurus* plant was discovered and selected by the Inventor as a single plant from within the progeny of the stated open-pollination in a controlled environment in Dayton, Oreg. during the autumn of 2010.

Asexual reproduction of the new *Laurus* plant by vegetative cuttings in a controlled greenhouse environment in Dayton, Oreg. since June, 2011 has shown that the unique features of this new *Laurus* plant are stable and reproduced true to type in successive generations.

SUMMARY OF THE INVENTION

The new *Laurus* plant has not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'MonRik'. These characteristics in combination distinguish 'MonRik' as a new and distinct *Laurus* plant:

1. Compact, upright to somewhat outwardly spreading and uniformly mounded plant habit.
2. Vigorous growth habit.
3. Freely branching habit.
4. Fragrant dark green-colored leaves.
5. Good garden performance.

Plants of the new *Laurus* differ from plants of the female parent selection primarily in plant size and habit.

Plants of the new *Laurus* can be compared to plants of unnamed selections of *Laurus nobilis* known to the Inventor, not patented. Plants of the new *Laurus* differ from plants of unnamed selections of *Laurus nobilis* known to the Inventor primarily in plant size and habit.

BRIEF DESCRIPTION OF THE PHOTOGRAPHS

The accompanying colored photographs illustrate the overall appearance of the new *Laurus* showing the colors as true as it is reasonably possible to obtain in colored reproductions of this type. Colors in the photographs may differ slightly from the color values cited in the detailed botanical description which accurately describe the colors of the new *Laurus*.

The photograph at the top of the sheet comprises a side perspective view of a typical plant of 'MonRik' grown in a container.

The photograph at the bottom of the sheet is a close-up view of typical leaves of 'MonRik'.

DETAILED BOTANICAL DESCRIPTION

The aforementioned photographs and following observations, measurements and values describe plants grown during the late autumn in two-gallon containers in an outdoor nursery in Dayton, Oreg. and under cultural practices typical of commercial *Laurus* production. During the production of the plants, day temperatures ranged from 10° C. to 32° C. and night temperatures ranged from −1° C. to 10° C. Plants were 2.5 years old when the photographs and the description were taken. In the description, color references are made to The Royal Horticultural Society Colour Chart, 2007 Edition, except where general terms of ordinary dictionary significance are used.

Botanical classification: *Laurus nobilis* 'MonRik'.

Parentage:

*Female, or seed, parent*.—Unnamed selection of *Laurus nobilis*, not patented.

*Male, or pollen, parent*.—Unknown selection of *Laurus nobilis*, not patented.

Propagation:

*Type*.—By vegetative cuttings.

*Time to produce a rooted young plant, summer*.—About one month at temperatures about 27° C.

*Time to produce a rooted young plant, winter*.—About two months at temperatures about 18° C.

*Root description*.—Medium in thickness, fibrous; white to yellow in color.

*Rooting habit*.—Moderately freely branching; medium density.

Plant description:

*Plant form and growth habit*.—Perennial; compact, upright to somewhat outwardly spreading and uniformly mounded plant habit; freely branching habit, about five to six primary lateral branches develop per plant; vigorous growth habit.

*Plant height*.—About 32 cm.

*Plant width* (*spread*).—About 35 cm.

*Lateral branches*.—Length: About 34 cm. Diameter: About 7 mm. Internode length: About 1.7 cm. Strength: Strong. Texture: Smooth, glabrous; becoming woody with development. Color, young stems: Close to 187A; color becoming closer to 147B with development. Color, woody stems: Close to N199A.

Leaf description:

*Arrangement*.—Alternate, simple.

*Length*.—About 7.7 cm.

*Width*.—About 2.2 cm.

*Shape*.—Narrowly elliptical.

*Apex*.—Acute.

*Base*.—Attenuate.

*Margin*.—Entire; crinkled.

*Texture, upper and lower surfaces*.—Smooth, glabrous; leathery and tough.

*Luster, upper surface*.—Slightly glossy.

*Luster, lower surface*.—Matte.

*Venation pattern*.—Pinnate.

*Fragrance*.—Mildly fragrant; bay-like, pleasant; suitable for culinary uses.

*Color*.—Developing leaves, upper surface: Close to 146C. Developing leaves, lower surface: Close to 146D. Fully expanded leaves, upper surface: Close to 146A; venation, close to 152B. Fully expanded leaves, lower surface: Close to 146B; venation, close to 152B and towards the petiole, close to 183B.

*Petioles*.—Length: About 6 mm. Diameter: About 2 mm. Texture, upper and lower surfaces: Smooth, glabrous. Color, upper surface: Close to 187B. Color, lower surface: Close to 187A.

Flower description: Flower initiation and development has not been observed on plants of the new *Laurus*.

Disease & pest resistance: Plants of the new *Laurus* have not been noted to be resistant to pathogens and pests common to *Laurus*.

Garden performance: Plants of the new *Laurus* have been observed to have good garden performance and tolerate rain, wind and suitable for USDA Hardiness Zones 8 through 11.

It is claimed:

1. A new and distinct *Laurus* plant named 'MonRik' as illustrated and described.

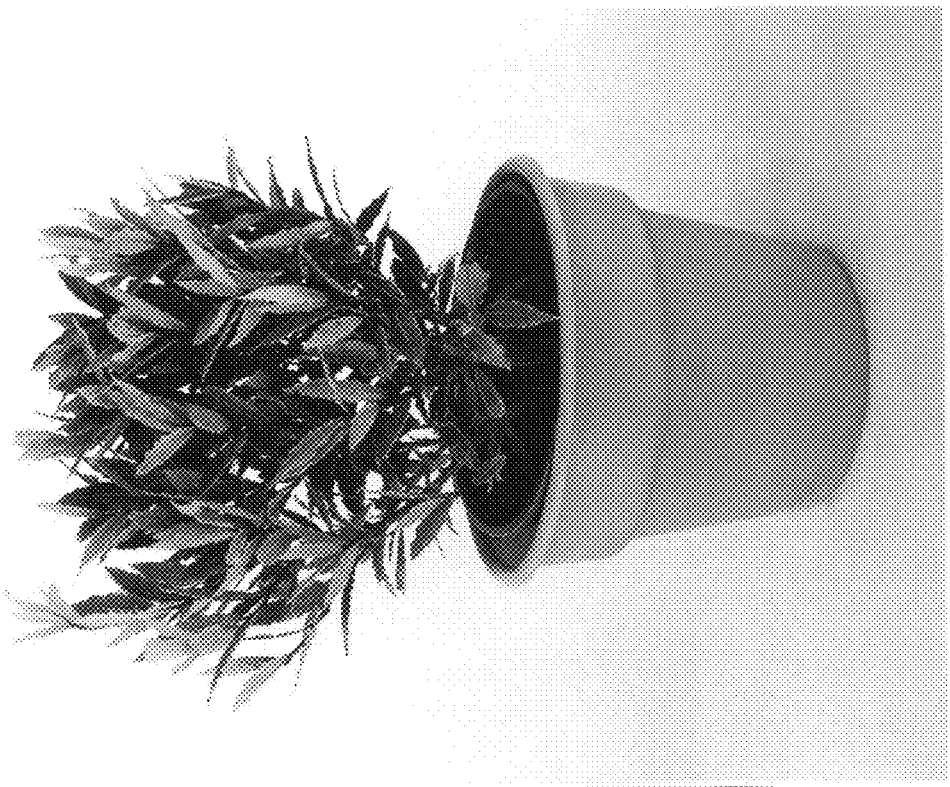
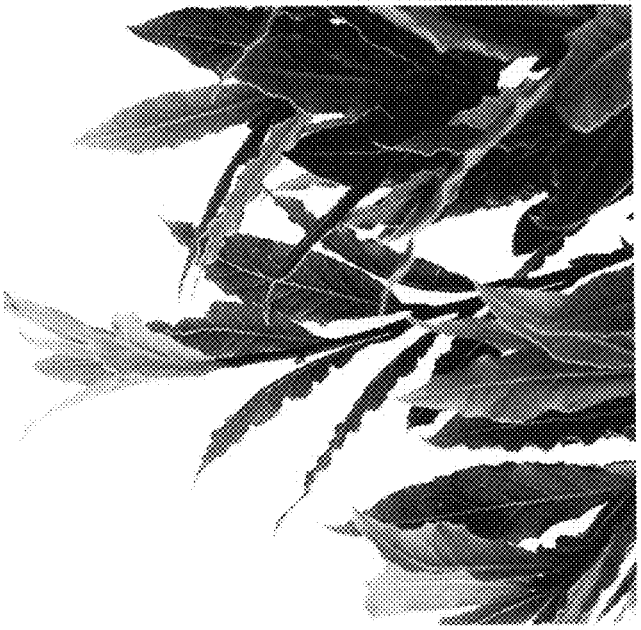

* * * * *